United States Patent [19]
Suzuki

[11] Patent Number: 5,931,782
[45] Date of Patent: Aug. 3, 1999

[54] METHOD AND APPARATUS FOR DETERMINING BY RADIATION DETECTION THE CONDITION AND FUNCTIONING OF A BODY UNDERGOING TEST AND A NOVEL EJECTION FRACTION METER

[75] Inventor: Arata Suzuki, deceased, late of Ramsey, N.J., by Marcia N. Suzuki, Administrator

[73] Assignee: Capintec, Inc., Ramsey, N.J.

[21] Appl. No.: 09/040,416

[22] Filed: Mar. 18, 1998

[51] Int. Cl.⁶ .................................................... G01J 1/02
[52] U.S. Cl. ................................................................ 600/436
[58] Field of Search ...................... 600/407, 436; 250/369, 370.08, 370.09

[56] References Cited

U.S. PATENT DOCUMENTS 5,742,060  4/1998  Ashburn ............................. 250/370.09
5,847,396  12/1998  Lingren et al. ......................... 250/369

*Primary Examiner*—George Manuel
*Attorney, Agent, or Firm*—Evenson, McKeown, Edwards & Lenahan, P.L.L.C.

[57] ABSTRACT

Counting rate measurements from radiation detectors are averaged and an index of the condition of a body, e.g. cardiac function of a patient by ejection fraction, is approximated as an inverse function of measurement averages, based on standard statistical deviation, to provide a continuous, real time evaluation of the condition, e.g. cardiac function. In the case of a patient, other patient measurement parameters establish limits within which the index of the condition, e.g. ejection fraction, approximations have acceptable accuracy.

16 Claims, 5 Drawing Sheets

METHOD AND APPARATUS FOR DETERMINING BY RADIATION DETECTION THE CONDITION AND FUNCTIONING OF A BODY UNDERGOING TEST AND A NOVEL EJECTION FRACTION METER

BACKGROUND AND SUMMARY OF THE INVENTION

This invention relates to a method and apparatus for monitoring and assessing the radiation emanated by a body undergoing test, such as, cardiac function monitoring and assessment, and more particularly, to a non-invasive system for determining the condition of the functioning of a patient's heart, and to a novel ejection fraction meter.

The use of radionuclide tracers and gamma radiation detectors to monitor cardiac function by gated blood pool volume measurement, is now generally well known and practiced in the field of nuclear medicine. Such a non-invasive system for monitoring and evaluating cardiac function is disclosed for example, in U.S. Pat. No. 5,072,458, which is a continuation-in-part of Ser. No. 07/096,521, filed Sep. 15, 1987, U.S. Pat. No. 5,007,427, which is a continuation-in-part of Ser. No. 07/046,854, filed May 7, 1987, U.S. Pat. No. 4,920,969, which is a division of Ser. No. 06/785,549, filed Oct. 8, 1985, now abandoned. According to the disclosure in this patent, an ambulatory nuclear detector has a physiological monitoring system associated therewith for evaluation of heart function by measurement of cardiac stroke volume relative to end diastolic volume, generally known as ejection fraction, deemed to be the best indicator of heart condition or cardiac function by non-invasive measurement means.

According to such prior systems for monitoring and evaluating cardiac function, in a non-invasive manner, intermittent readouts of ejection fraction is obtained by sampled measurements derived from an array of radiation detectors. Accordingly, the readout data on ejection fraction from such prior systems is in a converted digital format. Such prior systems for monitoring and evaluating cardiac function are sometime limited in use because of hardware complexities associated with data processing and data storage operations heretofore deemed necessary to obtain accurate data readout. Continuous, real time assessment of cardiac function with the desired degree of data accuracy has not, therefore, been available from non-invasive types of cardiac monitoring systems.

In addition to monitoring a body to determine cardiac function using tracers and gamma radiation detectors, there are similar situations regarding the measuring and testing of other bodies, such as therapeutic radionuclides, particularly, seeds used for implantation in prostate cancer and breast cancer, as well as possibly for removal of fat and plaque in cardiovascular disease. In one example, I-125 seeds for implantation are tested for asymmetry. The asymmetry or degree of same of such seed bodies is important information. Prior systems for developing such information are complex, and it is difficult to obtain accurate readout data by known prior art systems.

It is therefore an important object of the present invention to provide a method and apparatus for monitoring and evaluating a body undergoing test in a non-invasive manner on a continuous and real time basis.

A further object of the present invention is to provide a method and apparatus for monitoring and assessing cardiac function on a continuous and real time basis by readout of ejection fraction as an index or indicator of a patient's heart condition.

A still further object of the present invention is to provide a method and apparatus for monitoring and assessing therapeutic radionuclides to determine a property thereof, such as, asymmetry.

Another object of the present invention is to provide a novel efficacious ejection fraction meter.

SUMMARY OF THE INVENTION

In accordance with the present invention, the function of a body is monitored on a real time basis in terms of a property or condition of the body that is changing periodically, i.e., with time. For a special case, the cardiac function of a patient is monitored on a real time basis in terms of ejection fraction by detection of gamma radiation emitted from radioactive tracers introduced into the blood stream of the patient for such purpose. The signal output of the detectors, which may be mounted on the patient in accordance with the disclosure in the prior patent aforementioned, provides a continuous measurement of counting rate associated with the detected radiation more generally referred to as the occurrence of time-spaced events during a predetermined interval of time. A number of such counting rate measurements are averaged to provide a normal counting rate value from which the associated measurements deviate in accordance with a statistical characteristic. Such normal or averaged counting rate measurements therefore constitute an inverse function of an approximate ejection fraction value which may be calculated with a desired degree of accuracy by means of a novel mathematical algorithm or data processing program in order to achieve the data accuracy objective in accordance with an important discovery of the present invention.

In accordance with other discoveries of the present invention, the calculation of an approximate ejection fraction obtained from continuous, real time measurements has accuracy limits which may be established from data input obtained from the patient, such as the duration of the patient's respiratory cycle and heart beat cycle. Accuracy of the ejection fraction calculation is furthermore improved when the calculating operations are performed within limited time intervals, such as 0.5 seconds and averaged over longer time periods, such as 8 seconds. Facilities for limiting calculation of ejection fraction within the accuracy range and establishing accuracy limiting alarms or warnings, may also be provided.

In another special case, the asymmetry of I-125 seeds for implantation/therapy is determined by testing the seed bodies at a variety of angular orientations and times and calculating using the novel algorithm.

BRIEF DESCRIPTION OF DRAWING FIGURES

The foregoing objects, features and advantages of the invention, as well as others, will become apparent from the following detailed description of preferred embodiments when taken in conjunction with the accompany drawings, wherein.

DETAILED DESCRIPTION OF THE PREFERRED EMBODIMENT

Figure 1A:
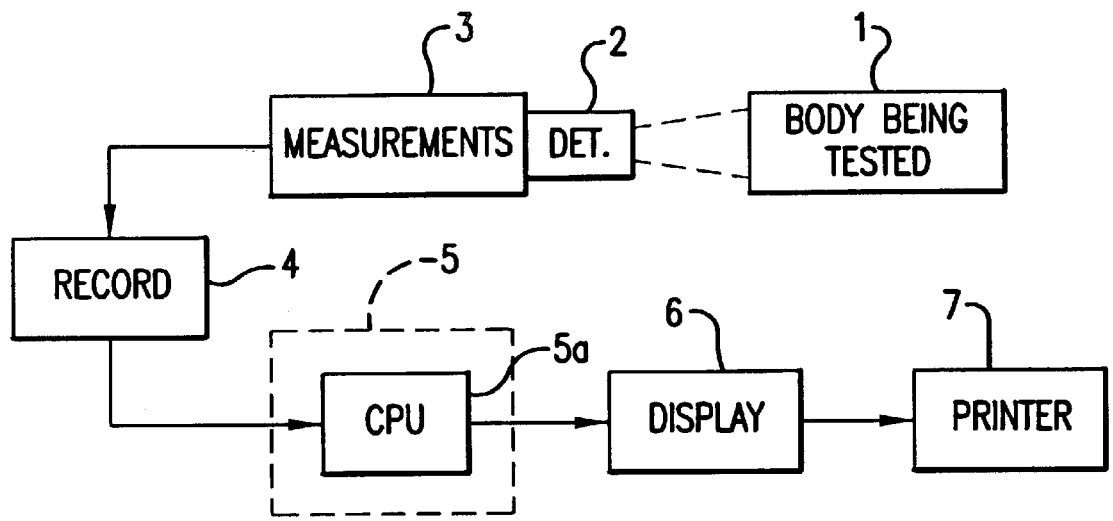
FIG. 1A is a block diagram of the novel method and apparatus of the present invention for monitoring a property of a body to determine a condition thereof.

Referring now to the drawings in detail, FIG. 1A illustrates, in block diagram, the novel method and apparatus of the present invention for monitoring a body 1 undergoing test. Body 1 may be the heart or some other part of a human or may be a therapeutic radionuclide or any other element, member, or material which changes periodically. The body emanates detectable energy in the form of radiation, such as, gamma rays which changes with time, or which changes due to a change in body orientation, e.g. rotation or angular position and therefore, time. A detector 2 suitable for detecting the energy emanating from body 1, detects same and block 3 determines the measure of same. If the energy is gamma rays, counts are detected per data point, e.g. 32 data points per second and over a period of time, e.g. 8 seconds. This data is recorded by conventional apparatus in block 4. The data in block 4 is fed to a computer 5 wherein it is processed in CPU 5a according to the novel algorithm of the present invention. The output of the computer 5 is fed to a display 6 and printer 7, as well as stored in the memory of computer 5.

The following equation constitutes the algorithm of the present invention and relates the measured values to the particular body property undergoing test:

$$\text{BODY PROPERTY} = \frac{2\sqrt{2} \cdot \sqrt{x^2 - 1}}{\left(\sqrt{\overline{C}} + \sqrt{2} \sqrt{x^2 - 1}\right) f}$$

where $f = 1 - B$ and B is the background radiation relative to the measured property; $x^2$ is a calculated value obtained from the number of data points and the counts per data point according to the following equation:

$$x^2 \equiv \frac{1}{N\overline{C}} \cdot \sum_{i=1}^{i=N} (\overline{C} - C_i)^2$$

where N equals number of data points per second times the number of seconds; C equals the counts per data point, and $\overline{C}$ equals the average of the counts per data point divided by the number of seconds of the period of time.

Figure 1B:
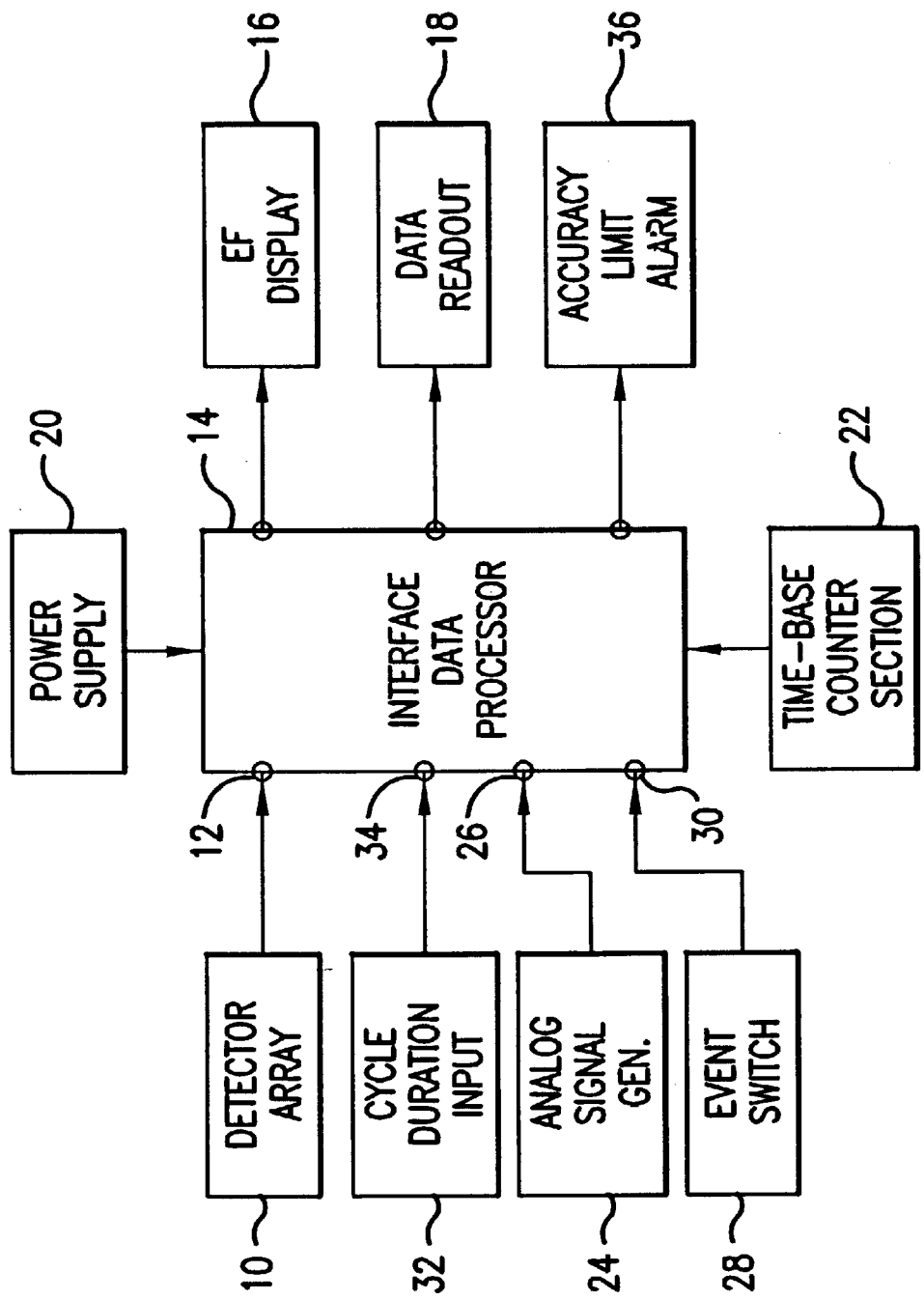
FIG. 1B is a schematic block diagram of the method and apparatus of the present invention for monitoring cardiac fraction including a novel ejection fraction meter.

Referring now to FIG. 1B, there is illustrated a method and apparatus according to the present invention for monitoring cardiac function of a human. An array of detectors 10 is placed non-invasively in close proximity to the body undergoing test, in this case, a heart in a human. Data detected by detectors 10, in the form of counts per second of emanating radiation, is fed to an input port 12 of an interface data processor 14 within which the data is processed and calculations performed on a continuous and real time basis in order to provide a readout to an ejection fraction display 16 and to other data readouts 18. The data processor 14 is powered through a power supply 20 and has a time based counter section 22 associated therewith through which the signal outputs from the detector array 10 are converted into counting rate measurements based on the radiation count output of the detectors during a predetermined time interval.

The radiation is created by injection of a suitable radionuclide. A source of analog signals from generator 24 connected to the data processor through input port 26, provides the signal base for the continuous, real time signal processing operations of the data processor. The operational mode of the data processor is determined by an input from event switch 28 connected to the input port 30. The calculating operations of the data processor, as will be explained hereinafter, are limited to an established accuracy range determined by data received from a source of cycle duration data 32 connected to input port 34 of the data processor as will also be further explained hereinafter. The system may also be provided with an alarm 36 through which indications may be provided that measurements are being made and read out is occurring under conditions exceeding accuracy limits.

Figure 2:
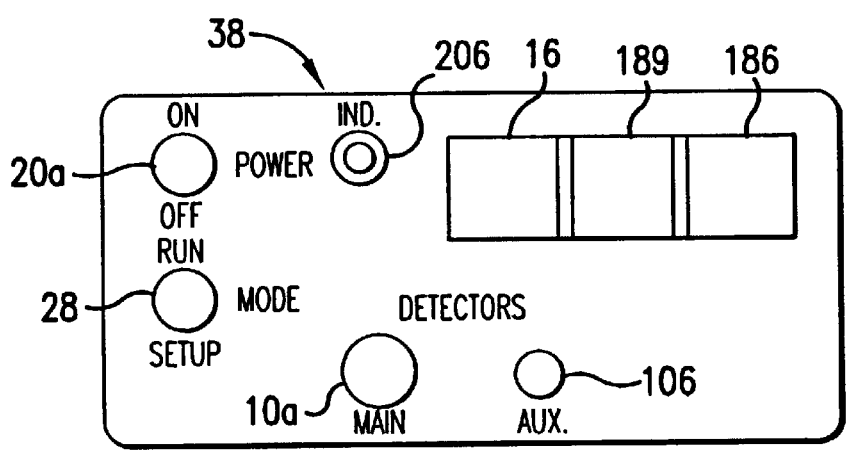
FIG. 2 is a front elevation view of a typical control and display panel of an ejection fraction meter in accordance with the present invention.

FIG. 2 illustrates by way of example a typical control and display panel of an ejection fraction meter generally referred to by reference numeral 38 embodying the system schematically depicted in FIG. 1. Associated with the power supply 20, is an on/off power switch 20a on the control panel of the meter as well as a power indicator lamp 20b, such as a light emitting diode. The event switch 28 is also shown in FIG. 2. the detector array, in accordance with one embodiment, may be that disclosed in the prior U.S. Pat. No. 5,072,458 aforementioned which is herein incorporated by reference, and includes a main detector adapted to be plugged into the connecting socket 10a in FIG. 2 as well as an auxiliary detector adapted to be plugged into the smaller connector socket 10b. The ejection fraction display 16 is disposed adjacent to two data readout displays 18a and 18b, respectively, indicating the actual counting rate measurements originating from the detectors and a normal or average counting rate value.

The data processor 14 hereinbefore described with respect to FIG. 1, performs a calculation algorithm or program in accordance with the present invention to provide an ejection fraction readout on display 16. Such readout is consistent with the generally known definition of ejection fraction (EF) in accordance with the following equation:

$$EF = \frac{D - S}{D - B}$$

where D and S are respectively end diastolic and end systolic counts while B is background radiation count.

The detector array 10 detects the radiation emanating from the heart under study or test at the rate of a preselected number of data points per second, preferably, 32 data points per second, and measures the total counts N of the detector array over a time period, preferably 8 seconds. The data processor is programmed to calculate according to the aforementioned algorithm to obtain values of the ejection fraction property of the heart (body). Thus, $$EF = \frac{2\sqrt{2} \cdot \sqrt{x^2 - 1}}{\left(\sqrt{\overline{C}} + \sqrt{2} \cdot \sqrt{x^2 - 1}\right) f}$$

where f=0.3 for a particular example and $$x^2 \equiv \frac{1}{N\overline{C}} \cdot \sum_{i=1}^{i=N} (\overline{C} - C_i)^2$$

There are certain limitations on the calculating operation capable of producing an ejection fraction approximation with an acceptable degree of accuracy. Since the measurements are derived from the detector positioned in operative relation to the left ventricle of the heart, heavy respiration could produce an inaccurate ejection fraction from the readout data. Accordingly, the counting rate measurements from which the ejection fraction calculation is derived, should be limited to a measurement period shorter than the duration of the respiratory cycles, but longer than the heartbeat cycles. Furthermore, it has been discovered that accurate measurement results are obtained, except during heavy exercise of the patient, by averaging the calculated ejection fractions over a period of 8 seconds. The accuracy of the ejection fraction approximation is furthermore improved by limiting the calculating operations to measurements obtained within time intervals under 0.5 seconds, that is updating at intervals less than 0.5 seconds.

Figure 3A:
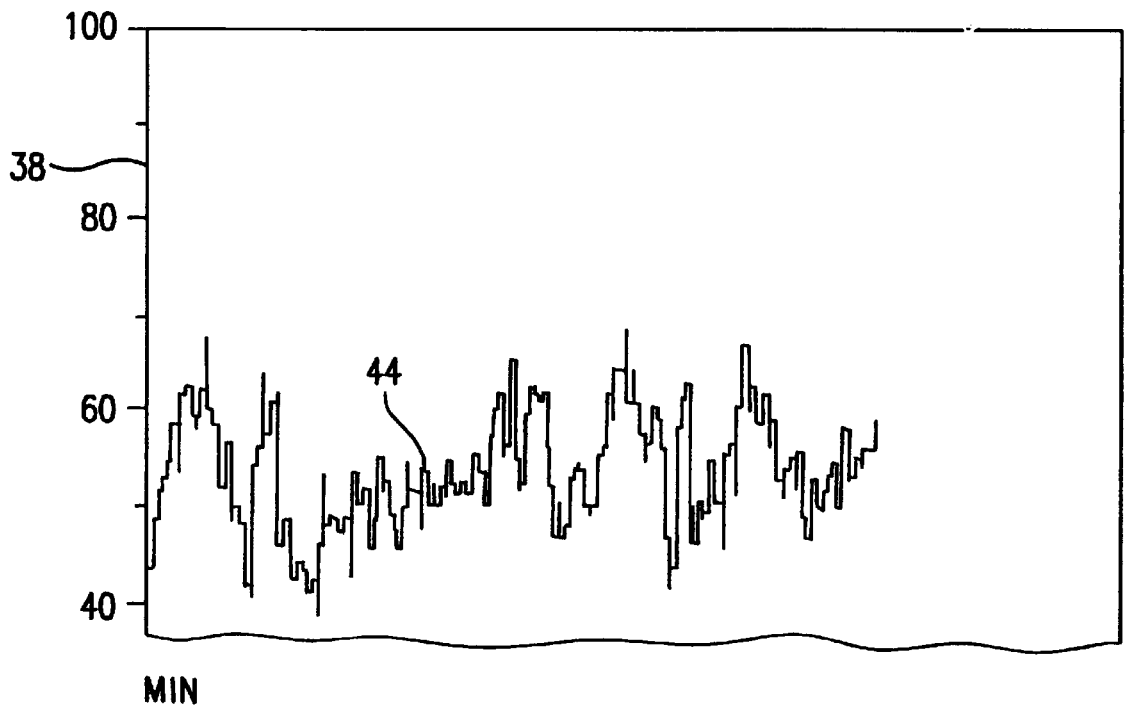
FIGS. 3A, 3B, 4A and 4B are comparative graphical illustrations of ejection fraction readout data demonstrating the efficacy of the system of the present invention.
Figure 3B:
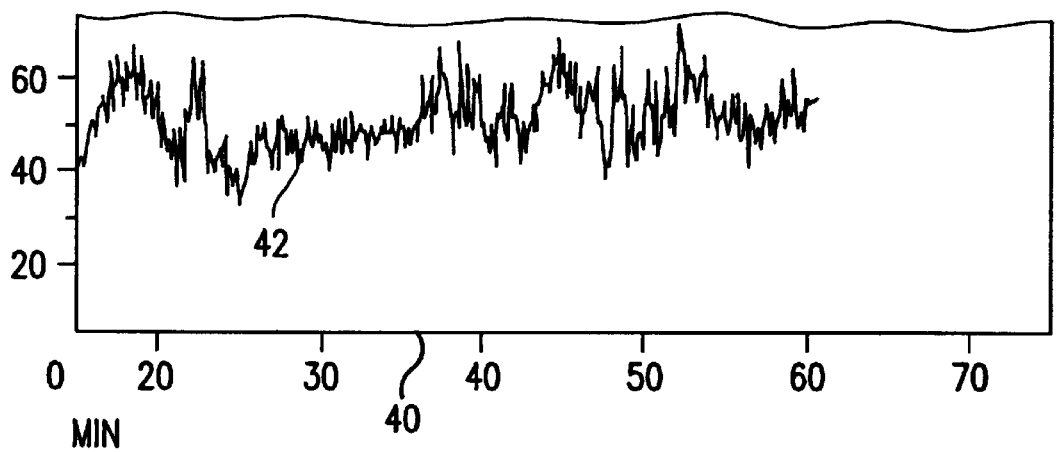
Figure 4A:
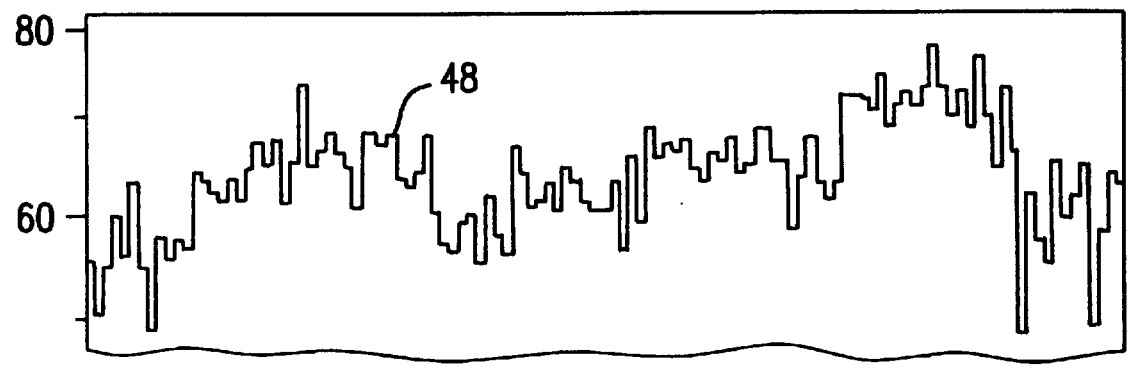
Figure 4B:
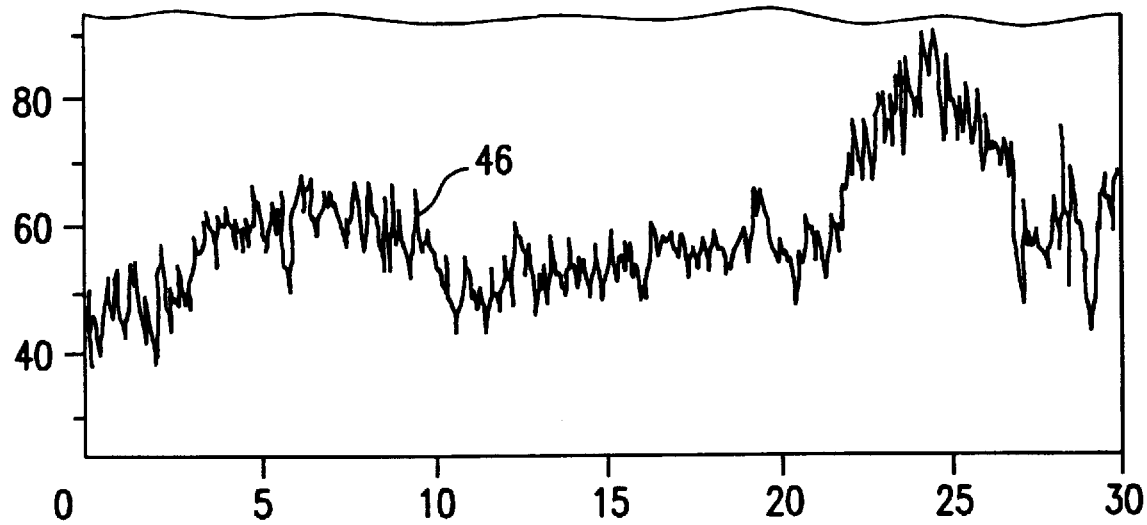

FIG. 3B illustrates graphically recorded readout of ejection fraction in accordance with the present invention, plotted as a curve 42 between an ordinate 38 representing ejection fraction in terms of percentage and an abscissa 40 in terms of minutes of time. A similar graphical readout of ejection fraction indicated by curve 44 in FIG. 3A, is obtained through prior systems, such as, by curve fitting, as the prior patent aforementioned. The ejection fraction curves 42 and 44 produced in accordance with the two different methods reflect cardiac function of a patient having unstable angina. The striking correlation between the curves 42 and 44 attest to the accuracy of the method and apparatus of the present invention in producing the ejection fraction readout curve 42. FIGS. 4B and 4A graphically illustrate curves 46 and 48 reflecting readouts of ejection fraction of a healthy patient, respectively produced, in accordance with the method and apparatus of the present invention and the system disclosed in the prior patent aforementioned. A comparison of curves 46 and 48 again shows correlation between cardiac function readout to demonstrate the accuracy of the data evaluating method and apparatus of the present invention.

Figure 5:
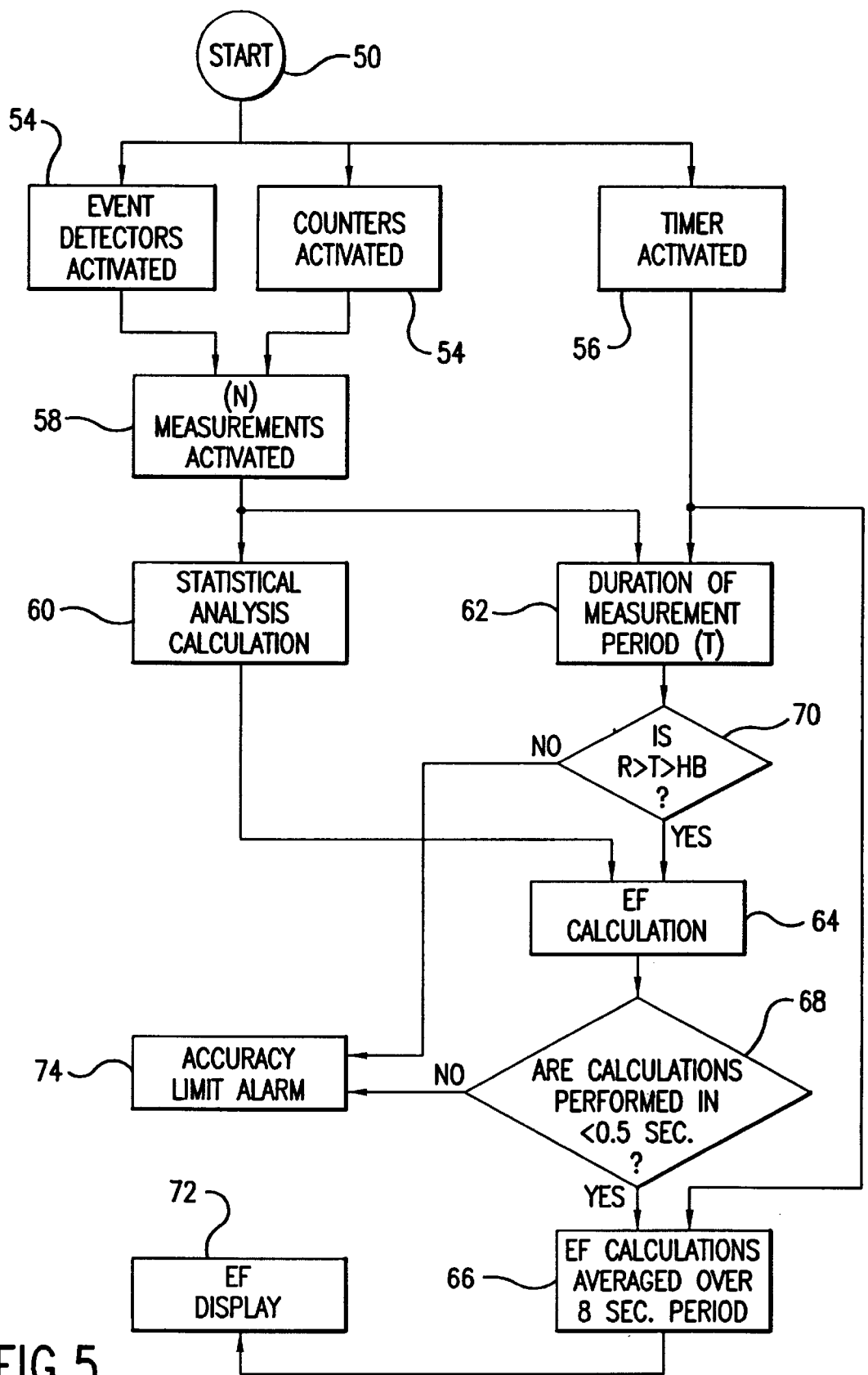
FIG. 5 is a flow chart associated with a typical data processing program associated with the present invention.

FIG. 5 is a flowchart illustrating a typical program to which operation of the data processor 14 is limited in order to carry out the method of the present invention. In response to a start step 50, event detectors, counters and timers are activated as indicated at 52, 54 and 56. The detectors and counters produce measurements which are averaged as indicated at 58. The averaged measurement data is fed to the data processor 14 and statistical analysis calculations, based on the novel algorithm given previously, are performed thereon on a continuous, real time basis as indicated at 60 while a simultaneous determination of the duration of the measurement input for each calculation is performed as indicated at 62. The output of such calculations proceeds to an ejection fraction approximation calculation at 64, based on the novel algorithm given previously. The output of such ejection fraction undergo an averaging step as indicated at 66, if the calculations are performed within a time limit as indicated by decision block 68. Only then, is the approximate ejection fraction output fed to the display 16 as indicated at 72. The ejection fraction calculation indicated at 64 is enabled, however, only if the duration of the measurements being utilized in the calculating operations are within the accuracy limits as indicated by the decision block 70. If the measurement duration is outside of such limits, then the accuracy limit alarm 36 is activated as indicated at 74. Such alarm is also activated if the calculations are performed during a period having a duration exceeding the prescribed limit as indicated at decision block 68.

The method and apparatus of the present invention contemplates the introduction of additional parameters to the data processor 14 through its input ports for specific monitoring and study purposes. Different types of data readout devices may also be added including recorders and data storage facilities. The additional input parameters may be the setting of initially expected ejection fraction or a constant fraction of averaged counts to be subtracted as background.

The monitoring and evaluating method and apparatus of the present invention has potential applications in connection with its ejection fraction readouts for the study and monitoring of interventions such as pre- and post-aortal coronary bypass surgery and angioplasty. The effects of medications and installation of pacemakers may also be monitored. The monitoring and evaluation operations of the present invention may also be readily utilized in recovery rooms, emergency rooms and various specialized medical units of a hospital or medical treating facility. Also, as previously noted, the invention has application to testing a body property which manifests by emanation of radiation.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed is:

1. A method for real time assessment of a condition reflected by time-spaced events, including the steps of:
   continuously detecting said time-spaced events;
   counting the number of said events detected during a predetermined time interval to obtain variable measurements;
   averaging said measurements to obtain a measurement average value with respect to which the measurements are distributed with standard statistical deviation; and
   calculating an approximate index of said condition as an inverse function of said measurement average value according to the following equations:

$$\text{INDEX} = \frac{2\sqrt{2} \cdot \sqrt{x^2 - 1}}{\left(\sqrt{\overline{C}} + \sqrt{2} \cdot \sqrt{x^2 - 1}\right)f}$$

where f=1 −B and B is the background radiation relative to the measurements and $x^2$ is determined according to the following equation:

$$x^2 \equiv \frac{1}{N\overline{C}} \cdot \sum_{i=1}^{i=N} (\overline{C} - C_i)^2$$

where N equals number of data points per second times the number of seconds; C equals the counts per data point; and $\overline{C}$ equals the average of the counts per data point divided by the number of seconds of the predetermined time interval.

2. The method of claim 1, wherein said condition is cardiac function of a patient and said index is ejection fraction.

3. The method of claim 2, including the steps of limiting said calculation of the approximate index to the measurements averaged during periods of time shorter in duration than the patient's respiratory cycle and longer in duration than the patient's heartbeat cycle.

4. The method of claim 3, wherein said detected events are signals generated by gamma radiation emitted by radioactive tracers.

5. The method of claim 1, wherein said detected events are signals generated by gamma radiation emitted by radioactive tracers.

6. The method of claim 1, wherein said condition is radioactivity of a therapeutic radionuclide seed and said index is asymmetry.

7. The method of claim 6, including the step of limiting said calculating step to counting rate measurements averaged during periods of time shorter in duration than the patient's respiratory cycle and longer in duration than the periodicity of the patient's cycle relative to said property.

8. A method for real time assessment of a function of a patient in terms of a property indicative of said function by detection of a counting rate of radiation from radioactive tracers, comprising the steps of:

continuously measuring said counting rate;

averaging statistically valid numbers of the counting rate measurements; and determining an approximation of said property as an inverse function of said averaged counting rate measurement.

9. Apparatus for realtime assessment of a condition of a body reflected by time-spaced events by detection of radiation from said body at a variable counting rate, comprising a device for continuously measuring said counting rate, a device for averaging said measured counting rate and a data processor for determining an approximation of an index of said condition as an inverse function of the averaged counting rate measurement.

10. Apparatus as defined in claim 9, including a device connected to the data processor for readout of said approximated index.

11. Apparatus as defined in claim 10, further including a device for measuring the duration of the patient's respiratory and heartbeat cycles and a data accuracy device connected to the cycle duration measuring device for limiting said readout of the approximated ejection fraction by the readout device.

12. Apparatus as defined in claim 9, wherein the condition is cardiac function and the index is ejection fraction.

13. An ejection fraction meter comprising a housing, a device mounted in said housing for receiving and averaging radiation detected measurements of a patient's cardiac function during a predetermined time interval to obtain a measurement average value with respect to which the measurements are distributed with standard statistical deviation, and a device for calculating ejection fraction as an inverse function of said measurement average value.

14. The ejection fraction meter according to claim 13, further including a device for limiting said calculation to measurements averaged during periods of time shorter in duration than the patient's respiratory cycle and longer in duration than the patient's heartbeat cycles.

15. The ejection fraction meter of claim 13, further including a readout device connected to the device for calculating ejection fraction for readout of said ejection fraction.

16. The ejection fraction meter of claim 13, wherein the device for calculating ejection fraction (EF) calculates according to the equations $$EF = \frac{2\sqrt{2} \cdot \sqrt{x^2 - 1}}{\left(\sqrt{\overline{C}} + \sqrt{2}\sqrt{x^2 - 1}\right)f}$$

where f=0.3 and $$x^2 \equiv \frac{1}{N\overline{C}} \cdot \sum_{i=1}^{i=N} (\overline{C} - C_i)^2$$

where N equals number of data points per second times number of records; C equals the counts per data point; and $\overline{C}$ equals the average of the counts per data point divided by the number of records of the period of time.

* * * * *